March 31, 1953 L. L. BROOKS Plant Pat. 1,175
AZALEA PLANT
Filed April 14, 1952
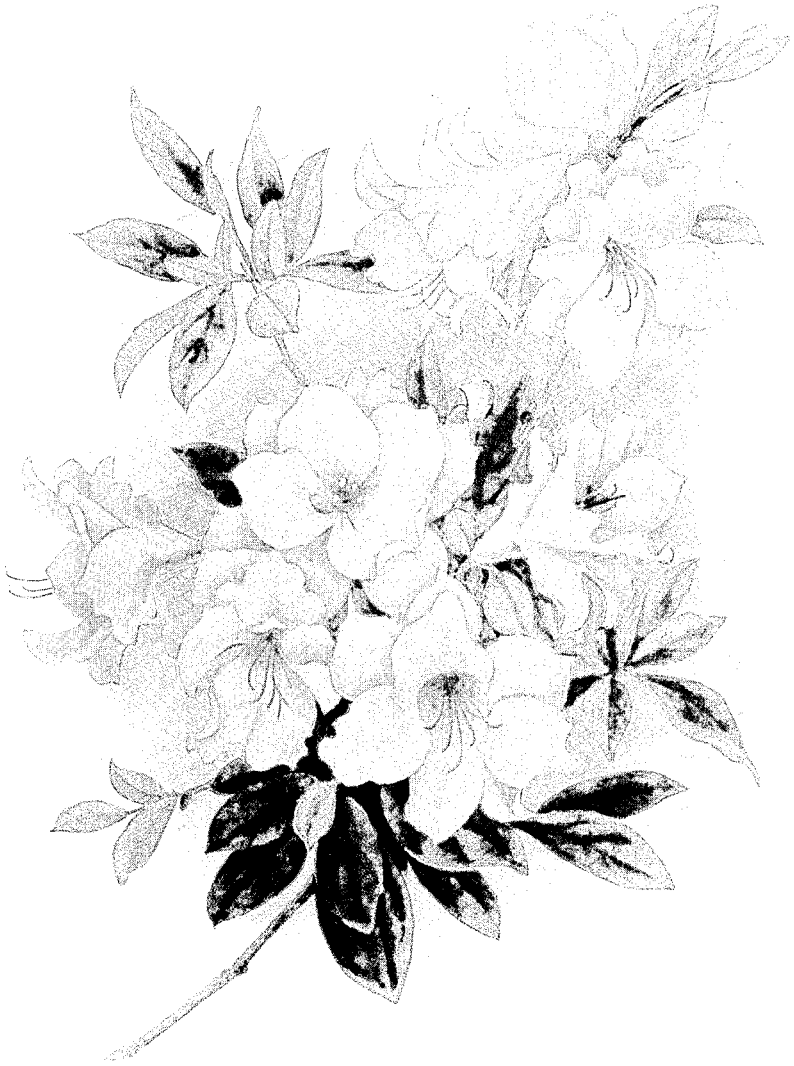
WITNESS
Addison E. Avery
INVENTOR
LENARD L. BROOKS
Webster & Webster
ATTYS.

Patented Mar. 31, 1953

Plant Pat. 1,175

UNITED STATES PATENT OFFICE 1,175

AZALEA PLANT

Lenard L. Brooks, Modesto, Calif.

Application April 14, 1952, Serial No. 282,206

1 Claim. (Cl. 47—60)

The present invention is directed to a new and distinct variety of azalea plant characterized by beautiful red flowers having an under-tone of orange, produced profusely on a plant of fine, uniformly compact growth habit. The under-tone of orange gives the flowers a brilliant, lively appearance that is of particular advantage under artificial light; the flowers being relatively large in size, with a normal Kurume type arrangement of the petals. The petals are relatively heavy, velvety inside and out, and somewhat ruffled.

A further important feature of the present invention of azalea plant is that the flowers are resistant to color fading and long lasting; the petals being persistent against wilting until the flowers are ready to fall.

In general, the herein claimed azalea plant is an excellent type for commercial use for the reason that—in addition to its beauty—it is easy to reproduce on its own roots; is a fine greenhouse-forcing quality; and also is valuable as a garden variety.

This variety was produced by me in the experimental garden of my nursery at Modesto, California; the variety being a cross made by pollen from the Kurume azalea Hexe used on the Belgian Indica azalea Wm. Van Orange, the parent varieties being unpatented.

Upon the cross being recognized as novel, and as it evidenced considerable value for commercial use, it was taken for propagation by cuttings, and such cuttings produced azalea plants which carried forward all of the new and distinct features of the original plant.

Such asexual reproduction of this variety by cuttings was carried out in my experimental garden located as aforesaid. Subsequent propagations of the variety by cuttings further evidence that such variety is fixed in its floricultural characteristics.

The figure of the drawing is a perspective view, on somewhat reduced scale, showing the flowers, together with twigs and leaves of the variety; the flowers here shown being of the color when the plant is grown outdoors, it being understood that the flowers—as well as the leaves—run to slightly deeper shades of color when greenhouse grown.

Referring now more specifically to the botanical details of this new and distinct variety of azalea plant, the following is an outline description thereof; all major color plate identifications being by reference to Maerz and Paul Dictionary of Color.

*Plant*

Form: Extremely freely branching; symmetrical; broader than tall, such tendency being maintained in the mature plant.

Growing habit: Dense and bushy, with medium sized leaves; the mature leaves being relatively heavy textured. The variety is a fast grower and produces market-sized budded plants in twelve to eighteen months from cuttings.

Blooming habit: By reason of the extremely free branching habit of the variety it produces more flowers than other azaleas in the general class. It flowers evenly over the entire plant, both on greenhous-forced plants and plants flowered naturally in the garden. From one to six flowers are produced on each stem.

Blooming season: March-April in central California. It is easily forced into flower, out of season, in the greenhouse.

Foliage:

*Size.*—Average ¾″ to 1¾″ in length and ⅜″ to ⅞″ in width.

*Color.*—Medium light yellowish green (19–L–7) in young leaves, with mature leaves shading from a medium green (20–L–7) to a darker green (23–L–8).

*Shape.*—Oval, pointed.

*Aspect.*—Glossy, nearly smooth.

*Texture.*—Relatively heavy in mature leaves.

*Edges.*—Smooth.

*Ribs and veins.*—Normal.

Flower:

*Size.*—Average, 2″ to 2¾″ in diameter.

*Borne.*—One to six on each stem.

*Stems.*—Medium length, inclined to droop due to the spreading habit of the plant.

*Form.*—Hose in hose.

*Permanence.*—Long lasting, with no fading or color change as the flowers age.

*Petalage.*—Five petals on each hose or flower.

*Color.*—Near cardinal red (1–J–5 to 1–J–6), with the upper part of the throat marked lightly with a deeper shade (1–L–6); there being an under-tone of orange (1–L–10) which imparts a very distinctive appearance to the flowers, especially under artificial light, as aforesaid.

Petals:

*Texture.*—Heavy.

*Appearance.*—Velvety, inside and out.

*Edges.*—Ruffled.

*Size.*—Average, 1¾″ to 2″ in length and ¾″ to 1″ in width.

*Shape.*—Ovate, oblong.

*Arrangement.*—Normal Kurume type; the inner hose or flower being set directly over the outer one.

*Persistence.*—Remains firm without wilting until flower is ready to fall.

Reproductive organs:

*Stamens.*—Five, two usually substantially shorter than the remainder.

*Pollen.*—White, not freely produced.

*Style.*—Well developed.

*Color.*—Deeper than the petals.

*Ovaries.*—Normal.

In comparison to other varieties of azalea plants the present variety somewhat resembles the Kurume variety Hexe, the pollen parent, but is principally distinguished as follows:

1. The flowers are larger and more freely produced.

2. The color is varied. The flowers of the herein claimed variety, while basically near-cardinal red, are characterized by their under-tone of orange, similar to the shade of the color found in the flowers of the Wm. Van Orange azalea plant, the seed parent. The advantage of this distinctive coloration, especially under artificial light, has heretofore been mentioned.

3. The leaves are smaller.

4. The plant is much less upright and branches better and more freely, thus producing more flowers.

It is indicated that the present variety has approximately the hardiness of the Hexe azalea and is equal or better for greenhouse forcing or garden culture; the variety—as with the Hexe—starting very easily from cuttings.

The plant and its flower herein described may vary in slight detail due to climatic and soil conditions under which the variety may be grown. For example, foliage color of an azalea is closely related to the conditions under which the plant is grown and the amount of acid used in its culture, and such color can thus vary substantially.

Having thus described the invention, I claim:

A new and distinct variety of azalea plant of the Kurume class comprised of a cross between the Kurume azalea Hexe and the Belgian Indica azalea Wm. Van Orange; characterized: by its extremely free branching, spreading habit, being less upright than the Hexe azalea but producing more and larger flowers, flowering evenly over the entire plant; by ruffled hose in hose flowers of near-cardinal red with an under-tone of orange, which flowers tend to droop by reason of such spreading habit of the plant; by its smaller leaves than the Hexe azalea; by its ease of reproduction on its own roots; by its excellence as a greenhouse-forcing and garden variety; and by its rapid growth from cutting to flowering plant.

LENARD L. BROOKS.

No references cited.